United States Patent [19]
Gregory et al.

[11] 4,215,686
[45] Aug. 5, 1980

[54] PCL FABRIC/FILM LAMINATE

[75] Inventors: John B. Gregory, Weyland; Arthur D. Schwope, Newton Lower Falls; Donald L. Wise, Belmont, all of Mass.

[73] Assignee: The United States of America as represented by the Secretary of the Navy, Washington, D.C.

[21] Appl. No.: 27,554

[22] Filed: Apr. 6, 1979

[51] Int. Cl.$^2$ .............................................. A61F 13/00
[52] U.S. Cl. ...................................... 128/156; 428/91
[58] Field of Search ................................ 128/155–156, 128/284–285, 290 R, 296; 428/91, 95, 97

[56] References Cited

U.S. PATENT DOCUMENTS

| 3,526,224 | 9/1970 | Potts | 128/156 |
|---|---|---|---|
| 3,561,441 | 2/1971 | Lombardi | 128/156 |
| 3,896,802 | 7/1975 | Williams | 128/156 |
| 3,903,882 | 9/1975 | Augurt | 128/155 |
| 3,949,742 | 4/1976 | Nowakowski | 128/155 |
| 3,967,623 | 7/1976 | Butterworth et al. | 128/287 |
| 4,034,751 | 7/1977 | Hung | 128/156 |
| 4,175,557 | 11/1979 | Hung | 128/156 |

OTHER PUBLICATIONS

J. Biomed. Mater. Res., II, pp. 489–502 (1977) Evaluation of Wound–Covering Materials.

Primary Examiner—C. Fred Rosenbaum
Attorney, Agent, or Firm—R. S. Sciascia; W. Thom Skeer; Lloyd E. K. Pohl

[57] ABSTRACT

An artificial burn covering comprising a poly($\epsilon$-caprolactone) film with a poly($\epsilon$-caprolactone) fabric attached thereto.

3 Claims, No Drawings

PCL FABRIC/FILM LAMINATE

BACKGROUND OF THE INVENTION

1. Field of the Invention

This invention relates to synthetic coverings for burn wounds. More specifically, this invention relates to synthetic coverings for burn wounds which will simulate skin and which may be applied for several days until grafting of the patients own skin may be carried out.

2. Description of the Prior Art

Typically, major burn wounds (second and third degree burns) have been covered with human or porcine skin for several days prior to grafting. Covering the wound with either of these materials for several days prepares the surface for autograft while protecting it from external bacteria intrusion.

Human and porcine skin are in short supply, are expensive and present major handling problems. Accordingly the need for synthetic replacements has been recognized. Among the replacements tested have been heat dried collagen/poly($\epsilon$-caprolactone) film laminates and freeze dried poly($\epsilon$-caprolactone) foam/poly($\epsilon$-caprolactone) film laminates. These replacements have been used with quite good success.

SUMMARY OF THE INVENTION

According to this invention, yet another suitable artificial burn covering is provided. The burn covering of this invention is a poly($\epsilon$-caprolactone) fabric/poly($\epsilon$-caprolactone) film laminate. The fabric portion of the laminate may be attached to the film portion by pressing it upon a tetrahydrofuran softened film.

DESCRIPTION OF THE PREFERRED EMBODIMENT

Poly($\epsilon$-caprolactone), hereinafter referred to as PCL, was spun into a fiber in a manner similar to that used in preparing nylon fiber. To do this a melt (PCL heated to a temperature of about 125° C.) was spun through a 68 orifice spinneret and then drawn with a draw ratio of about 4.7 to 1 to orient the fiber and reduce the cross section. This produced a yarn of about 120 to 140 denier.

The PCL yarn was then warp knitted into fabrics which, when brushed, produced piles resulting in open-looped velour/velvateen-type surfaces. Fabrics with five pile depths were prepared. Fabrics having naps of varying heights were produced. Among these were fabrics having a light nap of about 10 to 15 mils in height. This light nap fabric is preferred for use in practicing this invention.

A laminate of PCL fabric and a PCL film is used in practicing the invention. The laminate may be prepared by following the procedure set forth in the following example.

EXAMPLE

PCL (10g with an intrinsic viscosity of 1.15) was dissolved in 100 ml of tetrahydrofuran (THF) and the resulting solution was filtered through a 25 micron Teflon Millipore filter. A thoroughly cleaned glass plate was then provided and a film of PCL polymer solution was cast upon it using a Boston Bradley Blade set at 25 mils. The film was allowed to dry for 4+0.1 minutes. The non-napped side of the above-described PCL fabric was then gently pressed against the film to form a fabric/film laminate. The laminate was then peeled from the glass plate and residual THF was allowed to evaporate.

To test the laminates, the following experiment was carried out.

EXPERIMENT

Thirty two PCL fabric/PCL film laminates cut to approximately 2"×3" were placed (fabric side down) on full thickness excision wounds on the backs of 200–250 gram, male, Wister rats and held in place using 9mm stainless steel wound clips. Three days after grafting, the strength of the interfacial bonds that had developed between the wounds and the fabrics were measured using an Instron Model TT-C Tensile Tester. Prior to testing, the stainless steel clips were removed and the edges of the coverings were cut with scissors to produce even width strips about 2" wide. The coverings were removed at a rate of 3" per minute in a posterior anterior direction.

The experiment led to the important finding that while the degree of adhesion increased with the amount of nap in the fabric, a light nap (10 to 15 mils in height) appeared to optimum. With heavier naps, the fabric adhered too well so that a considerable amount of the new tissue formed beneath the covering was removed.

Water-loss rates of animals grafted with laminates of this invention are similar to those of animals with human cadaver skin grafts.

What is claimed is:

1. An article of manufacture comprising a poly($\epsilon$-caprolactone) film having affixed thereto a poly($\epsilon$-caprolactone) fabric having a non-napped side and a napped side, said non-napped side being affixed to said film.

2. An article of manufacture according to claim 1 wherein said film has a thickness of about 25 mils.

3. An article of manufacture according to claim 2 wherein said fabric has five pile depths and a light nap about 10 to 15 mils in height.

* * * * *